(12) United States Patent
Weiss

(10) Patent No.: US 11,925,497 B2
(45) Date of Patent: Mar. 12, 2024

(54) SYSTEMS, METHODS, AND DEVICES FOR MULTIPLE EXPOSURES IMAGING

(71) Applicant: Mazor Robotics Ltd., Caesarea (IL)

(72) Inventor: Noam Weiss, Haifa (IL)

(73) Assignee: Mazor Robotics Ltd., Caesarea (IL)

( * ) Notice: Subject to any disclaimer, the term of this patent is extended or adjusted under 35 U.S.C. 154(b) by 143 days.

(21) Appl. No.: 17/464,445

(22) Filed: Sep. 1, 2021

(65) Prior Publication Data

US 2023/0069629 A1 Mar. 2, 2023

(51) Int. Cl.
*G06T 5/50* (2006.01)
*A61B 6/00* (2006.01)
*G06T 5/00* (2006.01)

(52) U.S. Cl.
CPC .............. *A61B 6/52* (2013.01); *A61B 6/5241* (2013.01); *G06T 5/007* (2013.01); *G06T 5/50* (2013.01); *G06T 2207/10116* (2013.01)

(58) Field of Classification Search
CPC ......... A61B 6/52; A61B 6/405; A61B 6/5241; A61B 6/5258; A61B 6/5294; A61B 6/486; G06T 5/007; G06T 5/50; G06T 2207/10116
See application file for complete search history.

(56) References Cited

U.S. PATENT DOCUMENTS

| 6,243,440 | B1 | 6/2001 | Oikawa et al. |
| 7,471,768 | B2 | 12/2008 | Curtis et al. |
| 8,525,122 | B2 | 9/2013 | Chappo et al. |
| 9,204,849 | B2 | 12/2015 | Kurokawa et al. |
| 9,887,232 | B2 | 2/2018 | Kurokawa et al. |
| 10,357,214 | B2 | 7/2019 | Kimura et al. |
| 10,775,519 | B2 | 9/2020 | Dillen et al. |
| 2003/0191387 | A1 | 10/2003 | Petrick et al. |
| 2013/0077750 | A1* | 3/2013 | Yabugami .............. A61B 6/504 378/62 |
| 2020/0250814 | A1* | 8/2020 | Stoval, III ............... G06N 3/04 |

FOREIGN PATENT DOCUMENTS

CN 104545957 A * 4/2015

OTHER PUBLICATIONS

Translation of CN104545957A (Year: 2015).*
International Search Report and Written Opinion for International (PCT) Patent Application No. PCT/IL2022/050945, dated Nov. 30, 2022, 10 pages.

* cited by examiner

*Primary Examiner* — David P Porta
*Assistant Examiner* — Mamadou Faye
(74) *Attorney, Agent, or Firm* — Sheridan Ross P.C.

(57) ABSTRACT

Systems, methods, and devices for capturing a single image with multiple exposures is provided. An imaging device may be provided comprising a source configured to emit a wave for a time period and a detector configured to receive a signal indicative of the wave. A wave may be emitted for a time period and a signal may be received indicative of the emitted wave. A first image dataset may be saved with a first timestamp referencing a first time within the time period. A second image dataset may be saved with a second timestamp referencing a second time within the time period. The second time may occur after the first time.

16 Claims, 4 Drawing Sheets

SYSTEMS, METHODS, AND DEVICES FOR MULTIPLE EXPOSURES IMAGING

FIELD

The present technology generally relates to imaging with multiple exposures, and relates more particularly to capturing a single image with multiple exposures.

BACKGROUND

Imaging may be used by a medical provider for diagnostic and/or therapeutic purposes. Portions of a patient's anatomy may be visible under some image settings, but may not be visible under other image settings. As such, multiple images may be taken to obtain images of different portions of the patient's anatomy.

SUMMARY

Example aspects of the present disclosure include:

A system for capturing a single image with multiple exposures according to at least one embodiment of the present disclosure comprises an imaging device comprising a source configured to emit a wave for a time period and a detector configured to receive a signal indicative of the wave; at least one processor; and a memory storing data for processing by the processor, the data, when processed, causing the processor to: emit a wave for a time period; receive a signal indicative of the emitted wave; save a first image dataset with a first timestamp referencing a first time within the time period; and save a second image dataset with a second timestamp referencing a second time within the time period, the second time occurring after the first time.

Any of the aspects herein, wherein the first image dataset provides an image with a first exposure and the second image dataset provides an image with a second exposure, the first exposure being shorter than the second exposure.

Any of the aspects herein, wherein the memory stores further data for processing by the processor that, when processed, causes the processor to: transmit the first image dataset and the second image dataset after the time period; receive the transmitted first image dataset and the second image dataset; and combine the first image dataset and the second image dataset to form one image comprising image data with the first exposure and the second exposure.

Any of the aspects herein, wherein the detector is configured to absorb light, and wherein the first exposure corresponds to less light being absorbed than the second exposure, and wherein at least one object with a low attenuation is visible in the first image dataset having the first exposure and is fully saturated in the second image dataset.

Any of the aspects herein, wherein at least one object having a low attenuation is free of saturation in the first image dataset.

Any of the aspects herein, wherein the first time is after a beginning of the time period and prior to an end of the time period and the second time is after the end of the time period.

Any of the aspects herein, wherein the first image dataset and the second image dataset depict at least one anatomical element.

Any of the aspects herein, wherein the detector is configured to absorb light, and wherein the first image dataset corresponds to the detector absorbing light from a beginning of the time period to the first time and the second dataset correspond to the detector absorbing light from the beginning of the time period to the second time.

A system for capturing a single image with multiple exposures according to at least one embodiment of the present disclosure comprises an imaging device comprising a source configured to emit a wave for a time period and a detector configured to receive a signal indicative of the wave; at least one processor; and a memory storing data for processing by the processor, the data, when processed, causing the processor to: emit a wave for a time period; and receive a signal indicative of the emitted wave; and save a first image dataset having a first exposure; and save a second image dataset having a second exposure, the second exposure greater than the first exposure.

Any of the aspects herein, wherein the memory stores further data for processing by the processor that, when processed, causes the processor to: transmit the first dataset and the second dataset after the time period; receive the transmitted first image dataset and the second image dataset; and combine the first image dataset and the second image dataset to form one combined image comprising image data with the first exposure and the second exposure.

Any of the aspects herein, wherein at least one object is visible in the first image dataset and the one combined image and is fully saturated in the second image dataset.

Any of the aspects herein, wherein the detector is configured to absorb light, and wherein the first exposure corresponds to the detector absorbing light from a beginning of the time period to a first timestamp and the second exposure corresponds to the detector absorbing light from the beginning of the time period to a second timestamp, the first timestamp referencing a first time within the time period and the second timestamp referencing a second time within the time period, wherein the second time is after the first time.

Any of the aspects herein, wherein the imaging device comprises an X-ray device configured to use indirect conversion.

Any of the aspects herein, wherein the detector is configured to absorb light, and wherein the first image dataset corresponds to the detector absorbing light from a beginning of the time period to the first time and the second dataset correspond to the detector absorbing light from the beginning of the time period to the second time.

A device for combining multiple exposures according to at least one embodiment of the present disclosure comprises at least one processor; and memory storing instructions configured to cause a processor to: receive a first image dataset and a second image dataset, the first image dataset having a first exposure and the second image dataset having a second exposure, the second exposure greater than the first exposure; and combine the first image dataset and the second image dataset to form one combined image comprising image data with the first exposure and the second exposure.

Any of the aspects herein, wherein at least one object is visible in the first image dataset and is fully saturated in the second image dataset, and wherein the at least one object is visible in the one combined image.

Any of the aspects herein, wherein a first object having a low attenuation is depicted in the first dataset and a second object having a high attenuation is depicted in the second dataset, and wherein the first object and the second object are each depicted in the one combined image.

Any of the aspects herein, wherein combining the first image dataset and the second image dataset uses a combining model to yield the one combined image, the combining model trained using historical first image datasets and historical second image datasets.

Any of the aspects herein, wherein the first image dataset and the second image dataset are obtained during a single exposure from an imaging device.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
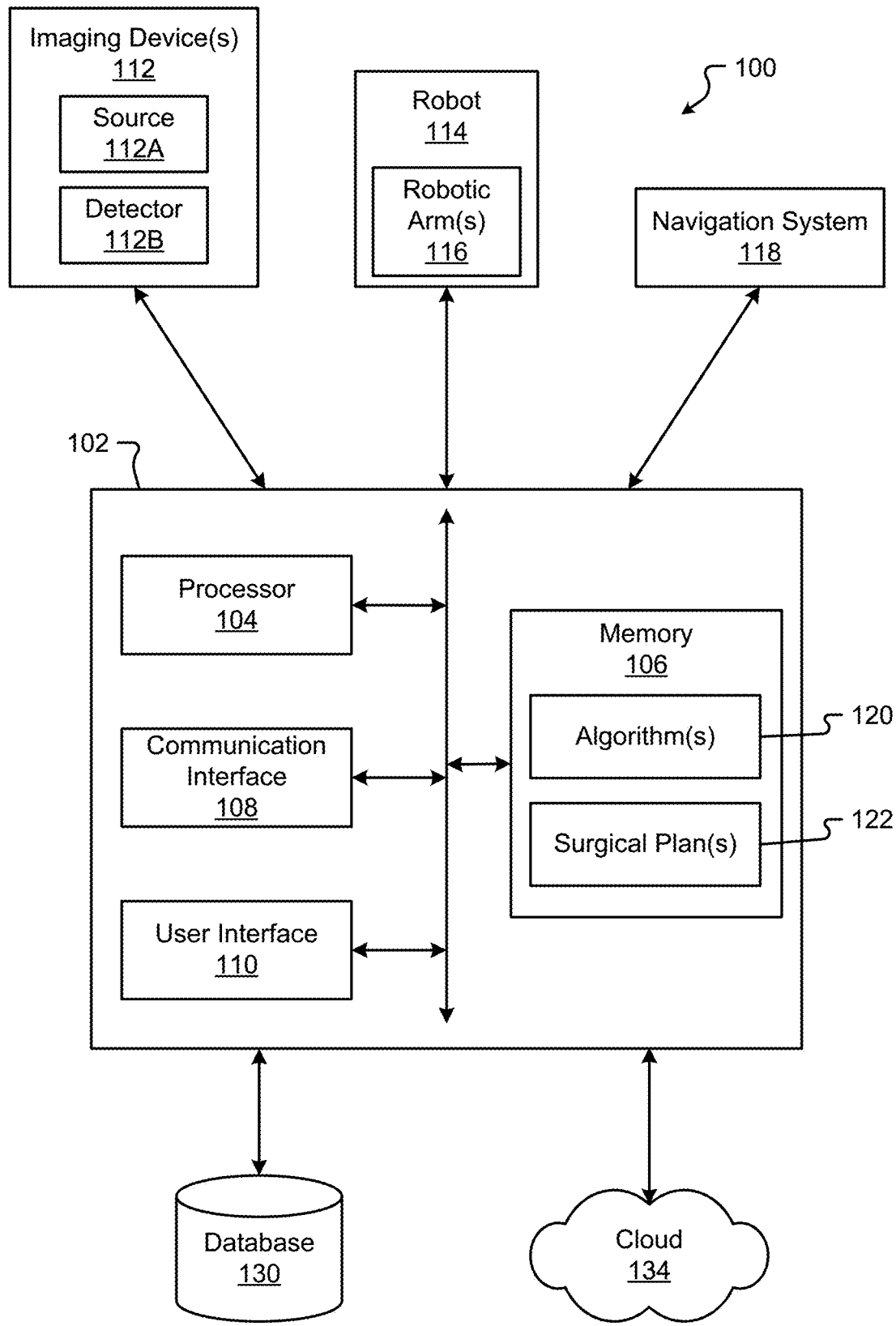
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

For some X-ray imaging applications, a dynamic range of a detector of an X-ray imaging device is very important. If the dynamic range is too small, some pixels within the detector may present value of zero (e.g., noise), if they are located behind a very attenuating object, which is the starvation limit. On the other hand, some pixels within the detector may present the maximal possible value (even if the true value of the measurement is higher), for example, in cases where the amount of radiation is too high — this is called the saturation limit.

By enlarging the dynamic range, more data can be gathered which results in improved images. One way for having more data is by taking two images—one with a lower exposure and one with a higher exposure. By having two sets of images, from one of the images it is possible to get the data of low attenuated pixels (which would not get saturated when working with lower exposure), and from another one of the images, it is possible to get data from very attenuating objects, when working with higher exposure. Conventional methods typically obtain these two images by exposing the patient to radiation twice — once to obtain one image and again to obtain another image.

At least one embodiment according to the present disclosure may comprise a detector operable to save two values for each pixel data. With such ability, it would be possible to save an image (e.g., a first set of values) after a very short time at a beginning of an X-ray pulse to get an image with lower radiation and to save a second image (e.g., a second set of values) at an end of the X-ray pulse. This could have all of the combined data, of a high and low exposure, from a single X-ray pulse. In other words, for a given spectrum, images of a higher and a lower exposure may be obtained. By enhancing the dynamic range, it would be possible to result in better reconstructed volume, more accurate planning, and safer clinical outcome.

Embodiments of the present disclosure provide technical solutions to one or more of the problems of (1) obtaining multiple image datasets within a single radiation exposure, (2) obtaining multiple image datasets with different exposures, and (3) increasing patient safety by reducing radiation exposure.

Turning first to FIG. 1, a block diagram of a system 100 according to at least one embodiment of the present disclosure is shown. The system 100 may be used to capture a single image with multiple exposures and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the method 400 described herein, or of any other methods. The memory 106 may store, for example, one or more algorithms 120 and/or one or more surgical plans 122. Such algorithms may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various method and features described herein. Thus, although various components of memory 106 are described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient.

In some embodiments, the imaging device 112 may comprise more than one imaging device 112. For example, a first imaging device may provide first image data and/or a first image at a first time, and a second imaging device may provide second image data and/or a second image at the first time or at a second time after the first time. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

In some embodiments, the imaging device 112 may comprise a source 112A and a detector 112B. In some embodiments, the source 112A and the detector 112B may be in separate housings or are otherwise physically separated. In other embodiments, the source 112A and the detector 112B may be in the same housing. The source 112A may be configured to emit a wave for a time period. The wave may be, for example, an X-ray wave. The detector 112B may be configured to receive a signal indicative of the emitted wave and to save a plurality of image datasets such as, for example, a first image dataset and a second image dataset, for a single emitted wave.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store, for example, one or more surgical plans 122 (including, for example, pose information for an imaging device 112; steps to capture one or more image datasets; one or more settings for an imaging device 112, etc.); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the method 400 described herein. The system 100 or similar systems may also be used for other purposes.

Figure 2:
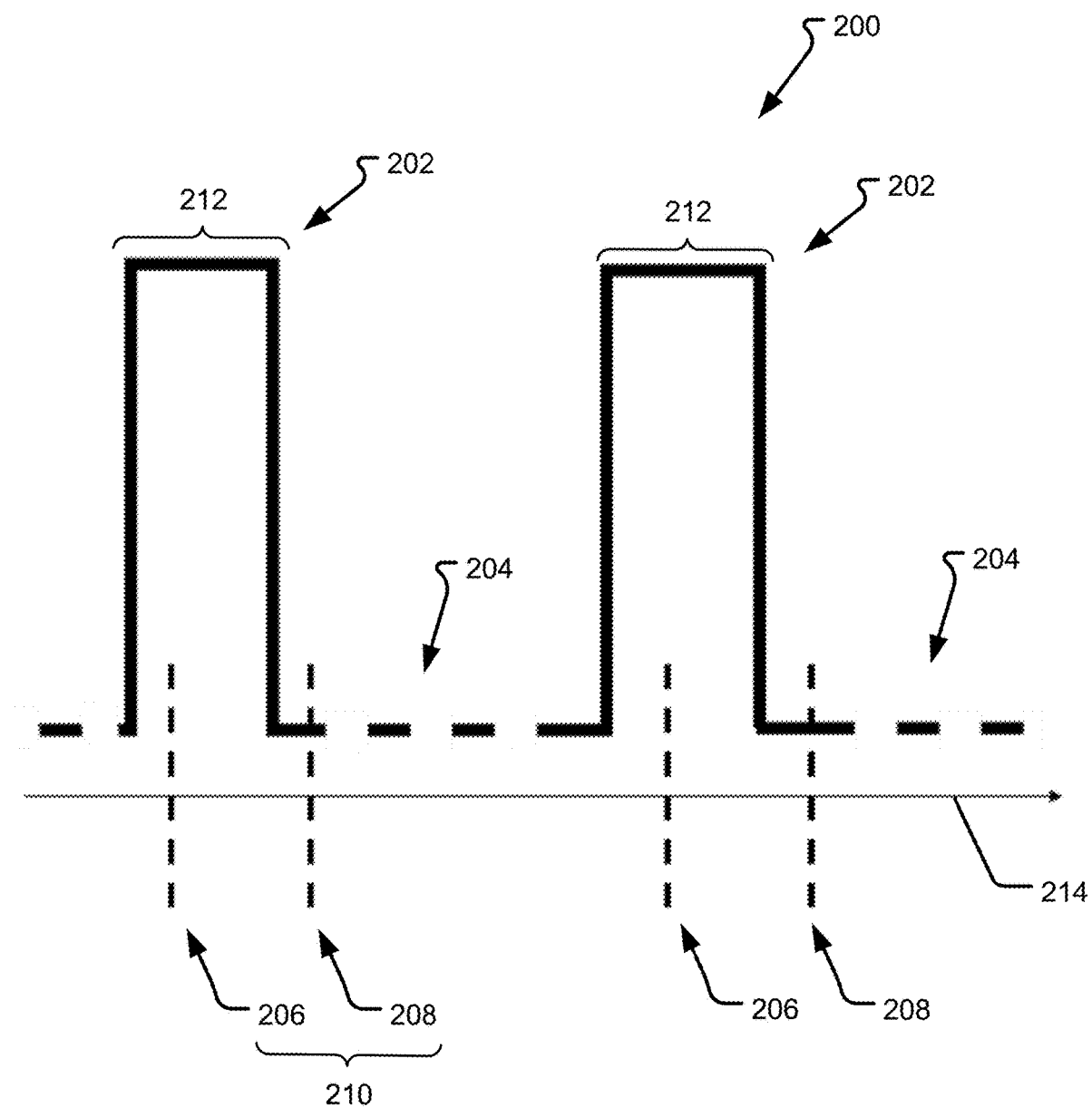
FIG. 2 is a schematic diagram of an example image data capturing time period according to at least one embodiment of the present disclosure.

FIG. 2 depicts a schematic diagram 200 of capturing a single image 210 having multiple exposures. The diagram 200 depicts when a wave is emitted from a source such as the source 112A, which will be referred to as an emitting stage 202, and when the wave is not emitted from the source, which will be referred to as an off stage 204, along a time axis 214. The wave may be emitted for a time period 212. During the time period 212, a detector such as the detector 112B may receive a signal indicative of the wave. The detector or a processor such as the processor 104—whether integrated with the detector or separate from the detector—may save a first image dataset at a first timestamp 206 and a second image dataset at a second timestamp 208. The first timestamp 206 may reference a first time within the time period and the second timestamp 208 may reference a second time within the time period. In some embodiments, the time between the first timestamp 206 and the second timestamp 208 may be equal to the time period 212. In other embodiments, the time between the first timestamp 206 and the second timestamp 208 may be greater than the time period 212. In still other embodiments, the time between the first timestamp 206 and the second timestamp 208 may be less than the time period 212.

As shown, the first timestamp 206 may be near a beginning of the time period 212 and during the emitting stage 202. In some embodiments, the first timestamp 206 may be at least prior to a halfway point in the time period 212. In other words, the first timestamp 206 may be within a first half of the time period 212. The second timestamp 208 may be near an end of the time period 212. In the illustrated embodiment, the second timestamp 208 is after the time period 212 or during the off stage 204, though in other embodiments the second timestamp 208 may be at or before an end of the time period 212.

Each of the plurality of image datasets may have an exposure level, which correlates to a time at which the signal is received. For example, an image dataset saved at a time near a beginning of the time period (e.g., the first timestamp 206) may have a lower exposure than an image dataset saved at a time near or after an end of the time period (e.g., the second timestamp 208). In some embodiments, the first image dataset may have a low exposure (e.g., the exposure may be of a low time period) and may depict one or more objects that are not saturated. The second image dataset may have a high exposure (e.g., the exposure may be of a time period longer than the low exposure) and may depict the one or more objects as fully saturated.

Figure 3A:
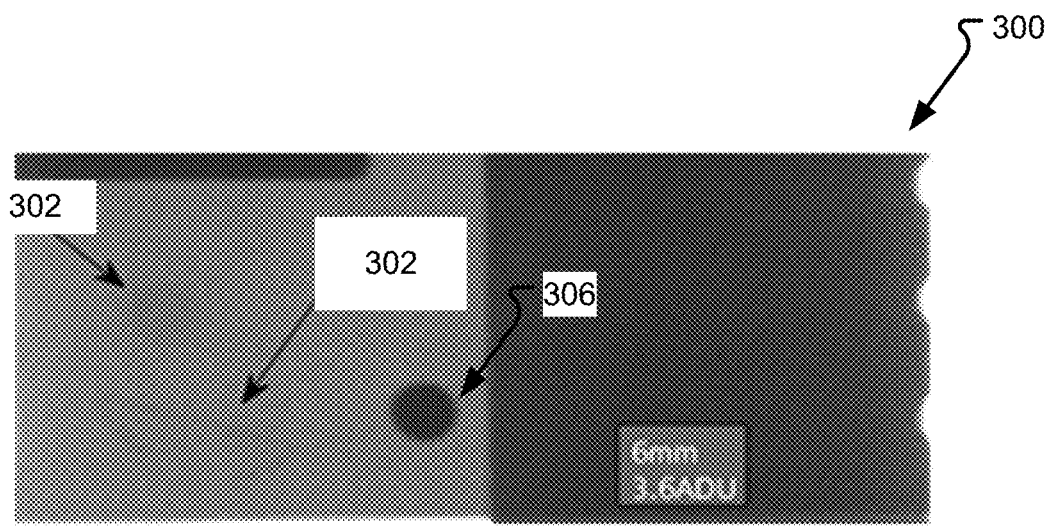
FIG. 3A is an example image having a first exposure according to at least one embodiment of the present disclosure.
Figure 3B:
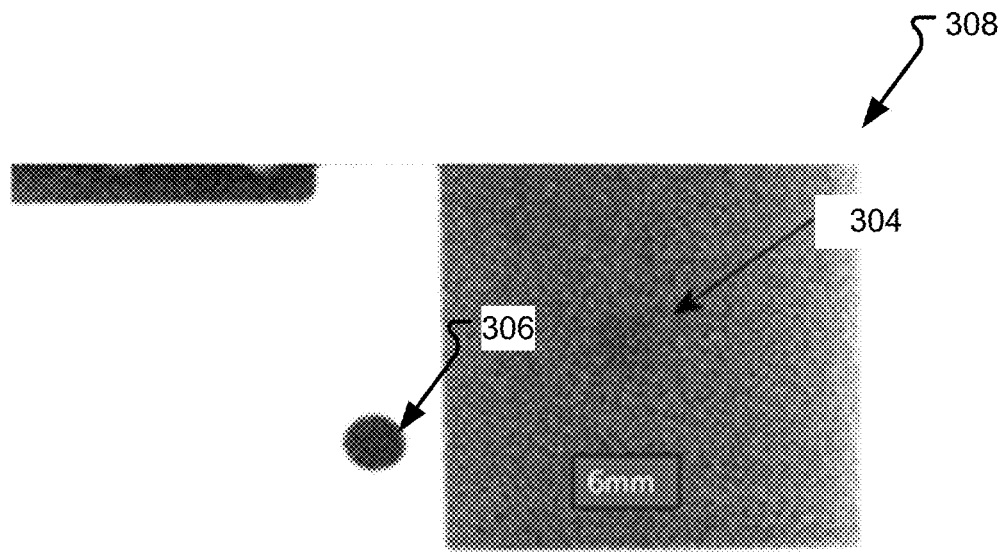
FIG. 3B is an example image having a second exposure according to at least one embodiment of the present disclosure.

FIGS. 3A and 3B depict an example first image 300 (which may be formed from, for example, a first image dataset) and an example second image 308 (which may be formed from, for example, a second image dataset), respectively. In the illustrated examples, the first image 300 and the second image 308 are the same image taken at a first timestamp and a second timestamp, respectively. The first timestamp is prior to or before the second timestamp and as such, the first image 300 has a lower exposure than the second image 308. As shown, objects 302 are visible in the first image 300 and are not visible in the second image 308, whereas the object 304 is visible in the second image 308 and is not visible in the first image 300. This is due to different levels of attenuation of each object. The objects 302 have a low level of attenuation and are visible in image data with lower exposure (e.g., the first image 300). The objects 302 become oversaturated and thus, are not visible, in image data with higher exposure (e.g., the second image 308). Whereas the object 304 has a high level of attenuation and is visible in image data with higher exposure (e.g., the second image 308) and are not visible in image data with lower exposure (e.g., the first image 300). Meanwhile, an object 306 has an attenuation level in which the object 306 is visible in both image data with lower exposure and higher exposure.

Capturing both the first image 300 and the second image 308 within a single emitted wave is beneficial in that objects that may only appear in image data with a lower exposure and objects that may only appear in image data with a higher exposure may both be captured at the same time while reducing an amount of radiation exposure to a patient. The image data of the lower exposure and the image data of the higher exposure may be combined to provide image data containing all objects visible in both sets of image data, as will be described in detail below.

Figure 4:
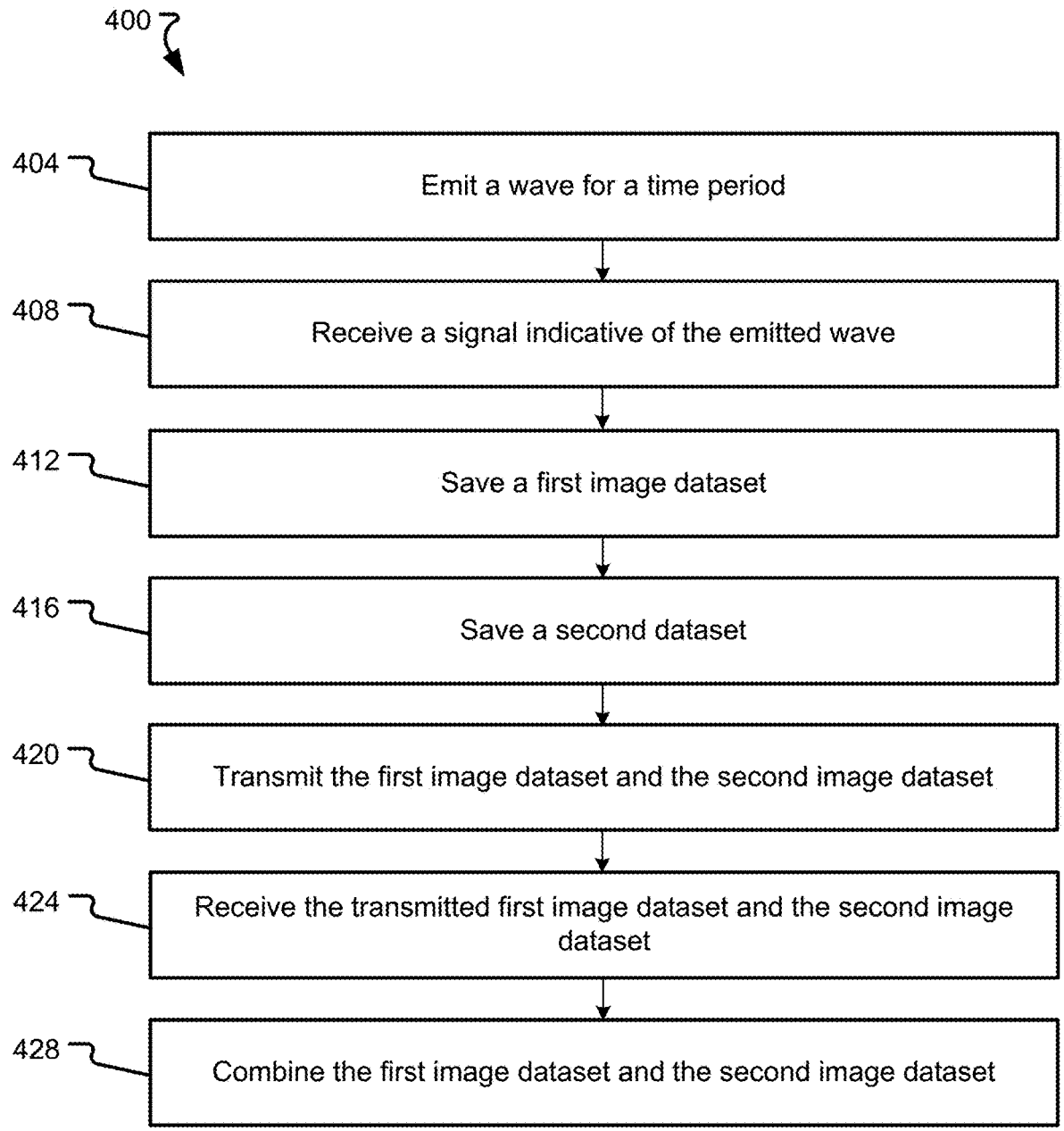
FIG. 4 is a flowchart according to at least one embodiment of the present disclosure.

FIG. 4 depicts a method 400 that may be used, for example, for capturing a single image having multiple exposures.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as the algorithm 120.

The method 400 comprises emitting a wave for a time period (step 404). The time period may be the time period 212. The wave may be emitted by a source such as the source 112A of an imaging device such as the imaging device 112. The wave may be, for example, an X-ray wave. The imaging device may be, for example, and X-ray device. The X-ray device, in some embodiments, is configured to use indirection conversion, though it will be appreciated that the X-ray device may be configured to use direct conversion.

The time period may be obtained from a surgical plan such as the surgical plan 122. In other instances, the time period may be input received from a user such as, for example, a surgeon, an X-ray technician, or other medical provider.

The method 400 also comprises receiving a signal indicative of the emitted wave (step 408). The signal may be received by, for example, a detector such as the detector 112B of the imaging device. The detector may be configured to receive the signal. The detector may also be configured to absorb light. More specifically, the detector may comprise a photodiode that measures visible light and converts the visible light to an electrical signal. The amount of time that the detector absorbs light correlates to a level or amount of exposure. The longer that light is absorbed—and thus, more light is absorbed—the higher the exposure level. Conversely, the shorted that light is absorbed—and thus, less light is absorbed—the lower the exposure level.

The method 400 also comprises saving a first image dataset (step 412). The first image dataset may be saved by a processor such as the processor 104. The processor may be integrated with the detector or separate from the detector. The first image dataset may be saved to a memory such as the memory 106, which may also be integrated with the detector or separate from the detector. The first image dataset may depict at least one anatomical element. The first image dataset is saved at a first timestamp, which references a first time within the time period of the wave. The first timestamp may be within the time period.

The method 400 also comprises saving a second image dataset (step 416). The second image dataset may be saved by the processor to the memory. In some embodiments, the second image dataset depicts the at least one anatomical element.

The second image dataset and the first image dataset may be each obtained during a single exposure from the imaging device. The second image dataset is taken at the same pose as the first image dataset. In other words, the second image dataset may depict the same image as the first image dataset, except that the second image dataset may be saved at a second timestamp. The second timestamp references a second time within the time period of the wave. In some embodiments, the second time occurs after the first time. The first time may be after a beginning of the time period and prior to an end of the time period or during the emitting stage 202. In some embodiments, the second time is after the end of the time period or during the off stage such as the off stage 204. In other embodiments, the second time may be at the end of the time period or prior to the end of the time period.

The first time and the second time may be obtained from a surgical plan such as the surgical plan 122. In other instances, the first time and the second time may be input from a user such as a surgeon or other medical provider. In some embodiments, the first time may be determined based on one or more objects, such as the objects 302, having a low attenuation. The first time may be set such that the one or more objects may be visible in the image data at the first time. The second time may be determined such that the image data at the second time has been exposed to the entire wave (or in other words, fully exposed).

In other instances, the first time and the second time may be determined by a processor such as the processor 104 executing a timestamp model. A type of imaging device, one or more imaging device settings, and/or a time period may be input into the timestamp model and the timestamp model may yield or output the first timestamp and the second timestamp. The timestamp model may be trained using historical image datasets (e.g., historical first image datasets and/or historical second image datasets) taken at historical timestamps (e.g., historical first timestamps and/or historical second timestamps). The timestamp model may be further trained using one or more historical imaging device settings.

The first image dataset provides an image with a first exposure and the second image dataset provides an image with a second exposure. In some embodiments, the first exposure may be less than the second exposure. In such instances, at least one object such as the objects 302 may have a low attenuation and may be visible in the first image dataset, but may be fully saturated (and thus, not visible) in the second image dataset. In other words, the at least one object having a low attenuation may be free of saturation in the first image dataset. Similarly, at least one object such as the object 304 may have a high attenuation and may be visible in the second image dataset, but may not be visible in the first image dataset.

The method 400 also comprises transmitting the first image dataset and the second image dataset (step 420). In some embodiments, the first image dataset and the second image dataset may be transmitted after the time period has elapsed. In other embodiments, the first image dataset and/or the second image dataset may be transmitted during the time period. In still other embodiments, the first image dataset may be transmitted during the time period and the second image dataset may be transmitted after the time period.

In some embodiments, the first image dataset and the second image dataset may be transmitted by a processor of the imaging device to another processor. In other embodiments, the first image dataset and the second image dataset may be transmitted by a processor separate from the imaging device to another processor. It will be appreciated that in some embodiments, the step 420 may be omitted from the method 400.

The method 400 also comprises receiving the first image dataset and the second image dataset (step 424). The first image dataset and the second image dataset may be received by a processor such as the processor 104 of a computing device such as the computing device 102. In such instances, the processor may receive the first image dataset and the second image dataset from a processor of the imaging device or from a processor separate from the imaging device. It will be appreciated that in some embodiments, the step 424 may be omitted from the method 400.

It will also be appreciated that in some embodiments, the steps 420 and 424 may occur prior to steps 412 and/or 416. For example, the first image dataset may be transmitted from the detector, received by a processor of, for example, the computing device, and saved by the processor to memory.

The method 400 also comprises combining the first image dataset and the second image dataset (step 428). The first image dataset and the second image dataset may be combined to form one image comprising image data of the first exposure and the second exposure. The combined image may depict objects that were previously visible in the first image dataset, but not the second image dataset, and vice versa. For example, at least one object such as the object 302 may be visible in the first image dataset and the combined image, but fully saturated in the second image dataset (and thus, not visible). In another example, at least one object such as the object 306 may be visible in the second image dataset and the combined image, but may not be visible in the first image dataset.

The combined image may be generated by a processor such as the processor 104 executing a combining model. The first image dataset, the second image dataset, the first time, the second time, the imaging device, and/or one or more imaging device settings may be input into the combining model and the combining model may yield or output the combined image. The combining model may be trained using historical image datasets (e.g., historical first image datasets and/or historical second image datasets) taken at historical timestamps (e.g., historical first timestamps and/or historical second timestamps). The combining model may be further trained using one or more historical imaging device settings.

It will be appreciated that step 428 may, in some embodiments, occur after step 416. In other words, step 428 may occur without steps 420 and/or 424.

The present disclosure encompasses embodiments of the method 400 that comprise more or fewer steps than those described above, and/or one or more steps that are different than the steps described above.

As noted above, the present disclosure encompasses methods with fewer than all of the steps identified in FIG. 4 (and the corresponding description of the method 400), as well as methods that include additional steps beyond those identified in FIG. 4 (and the corresponding description of the method 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for capturing a single image with multiple exposures comprising:
   an imaging device comprising a source configured to emit a wave for a time period and a detector configured to receive a signal indicative of the wave, the detector configured to absorb light;
   at least one processor; and
   a memory storing data for processing by the processor, the data, when processed, causing the processor to:
      emit a wave for a time period;
      receive a signal indicative of the emitted wave;
      save a first image dataset with a first timestamp referencing a first time within the time period; and save a second image dataset with a second timestamp referencing a second time within the time period, the second time occurring after the first time, wherein the first image dataset provides an image with a first exposure and the second image dataset provides an image with a second exposure, the first exposure being shorter than the second exposure, wherein the first exposure corresponds to less light being absorbed than the second exposure, and wherein at least one object with a low attenuation is visible in the first image dataset having the first exposure and is fully saturated in the second image dataset.

2. The system of claim 1, wherein the memory stores further data for processing by the processor that, when processed, causes the processor to: transmit the first image dataset and the second image dataset after the time period; receive the transmitted first image dataset and the second image dataset; and combine the first image dataset and the second image dataset to form one image comprising image data with the first exposure and the second exposure.

3. The system of claim 1, wherein the at least one object having the low attenuation is free of saturation in the first image dataset.

4. The system of claim 1, wherein the first time is after a beginning of the time period and prior to an end of the time period and the second time is after the end of the time period.

5. The system of claim 1, wherein the first image dataset and the second image dataset depict at least one anatomical element.

6. The system of claim 1, wherein the first image dataset corresponds to the detector absorbing light from a beginning of the time period to the first time and the second dataset correspond to the detector absorbing light from the beginning of the time period to the second time.

7. The system of claim 1, wherein a timestamp model is configured to yield the first timestamp and the second timestamp, wherein the timestamp model is trained using historical first image datasets taken at historical first timestamps and historical second image datasets taken at historical second timestamps.

8. A system for capturing a single image with multiple exposures comprising:

an imaging device comprising a source configured to emit a wave for a time period and a detector configured to receive a signal indicative of the wave;

at least one processor; and a memory storing data for processing by the processor, the data, when processed, causing the processor to:

emit a wave for a time period; and receive a signal indicative of the emitted wave; and save a first image dataset having a first exposure; and save a second image dataset having a second exposure, the second exposure greater than the first exposure, wherein at least one object is visible in the first image dataset and the one combined image and is fully saturated in the second image dataset.

9. The system of claim 8, wherein the memory stores further data for processing by the processor that, when processed, causes the processor to:

transmit the first image dataset and the second image dataset after the time period;

receive the transmitted first image dataset and the second image dataset; and combine the first image dataset and the second image dataset to form one combined image comprising image data with the first exposure and the second exposure.

10. The system of claim 8, wherein the detector is configured to absorb light, and wherein the first exposure corresponds to the detector absorbing light from a beginning of the time period to a first timestamp and the second exposure corresponds to the detector absorbing light from the beginning of the time period to a second timestamp, the first timestamp referencing a first time within the time period and the second timestamp referencing a second time within the time period, wherein the second time is after the first time.

11. The system of claim 8, wherein the imaging device comprises an X-ray device configured to use indirect conversion.

12. The system of claim 8, wherein the detector is configured to absorb light, and wherein the first image dataset corresponds to the detector absorbing light from a beginning of the time period to the first time and the second dataset correspond to the detector absorbing light from the beginning of the time period to the second time.

13. A device for combining multiple exposures comprising:

at least one processor; and memory storing instructions configured to cause a processor to:

receive a first image dataset and a second image dataset, the first image dataset having a first exposure and the second image dataset having a second exposure, the second exposure greater than the first exposure; and combine the first image dataset and the second image dataset to form one combined image comprising image data with the first exposure and the second exposure, wherein at least one object is visible in the first image dataset and is fully saturated in the second image dataset, and wherein the at least one object is visible in the one combined image.

14. The device of claim 13, wherein a first object having a low attenuation is depicted in the first dataset and a second object having a high attenuation is depicted in the second dataset, and wherein the first object and the second object are each depicted in the one combined image.

15. The device of claim 13, wherein combining the first image dataset and the second image dataset uses a combining model to yield the one combined image, the combining model trained using historical first image datasets and historical second image datasets.

16. The device of claim 13, wherein the first image dataset and the second image dataset are obtained during a single exposure from an imaging device.

* * * * *